(12) United States Patent
Mu et al.

(10) Patent No.: US 12,256,988 B2
(45) Date of Patent: Mar. 25, 2025

(54) SEMICONDUCTOR LASER MODULE AND METHOD FOR APPLICATION IN NONINVASIVE MEDICAL TREATMENT

(71) Applicant: Focuslight Technologies Inc., Xi'an (CN)

(72) Inventors: Mingang Mu, Xi'an (CN); Kai Yang, Xi'an (CN); Qiang Wang, Xi'an (CN); Lei Cai, Xi'an (CN); Jianfei Mu, Xi'an (CN); Xuejie Liang, Xi'an (CN); Xiaorong Xing, Xi'an (CN); Xingsheng Liu, Xi'an (CN)

(73) Assignee: Focuslight Technologies Inc., Xi'an (CN)

( * ) Notice: Subject to any disclaimer, the term of this patent is extended or adjusted under 35 U.S.C. 154(b) by 188 days.

(21) Appl. No.: 16/341,937

(22) PCT Filed: Sep. 28, 2017

(86) PCT No.: PCT/CN2017/104023
§ 371 (c)(1),
(2) Date: Apr. 15, 2019

(87) PCT Pub. No.: WO2018/072610
PCT Pub. Date: Apr. 26, 2018

(65) Prior Publication Data
US 2019/0239951 A1    Aug. 8, 2019

(30) Foreign Application Priority Data

Oct. 17, 2016    (CN) .......................... 201610901567.5
Oct. 17, 2016    (CN) .......................... 201621127578.4

(51) Int. Cl.
*A61B 18/20*     (2006.01)
*A61N 5/06*      (2006.01)
*A61B 18/00*     (2006.01)

(52) U.S. Cl.
CPC .......... *A61B 18/203* (2013.01); *A61N 5/0616* (2013.01); *A61B 2018/00047* (2013.01);
(Continued)

(58) Field of Classification Search
CPC ........ A61N 5/0616; A61B 2018/20533; A61B 2018/18203
See application file for complete search history.

(56) References Cited

U.S. PATENT DOCUMENTS 5,870,133 A  *  2/1999  Naiki ..................... G02B 7/028
                                                           347/247
6,332,688 B1 *  12/2001  Magarill ................ H04N 9/315
                                                           362/302
(Continued)

FOREIGN PATENT DOCUMENTS

CN        200941530 Y        8/2007
CN        201230700 Y        5/2009
(Continued)

*Primary Examiner* — Jennifer Pitrak McDonald
*Assistant Examiner* — Jennifer L Ghand
(74) *Attorney, Agent, or Firm* — IPro, PLLC

(57)         ABSTRACT

The present invention provides a semiconductor laser module and a method for application in noninvasive medical treatment. The module comprises a direct-output type semiconductor laser light source and a beam shaping device disposed in the light-exit direction of the direct-output type semiconductor laser light source. The beam shaping device comprises a light reflection component. The light reflection component is configured to enable laser beams outputted by the direct-output type semiconductor laser light source to be uniform. Based on the semiconductor laser module and the method provided in the present invention, the objective of treatment can be achieved by means of extracorporeal irradiation in a case in which no harm is done to a human body, costs are low, and the treatment effect is good.

10 Claims, 6 Drawing Sheets

(52) U.S. Cl.
CPC ............... *A61B 2018/00464* (2013.01); *A61B 2018/00642* (2013.01); *A61B 2018/00791* (2013.01); *A61B 2018/20553* (2017.05)

(56) References Cited

U.S. PATENT DOCUMENTS

| | | | | |
|---|---|---|---|---|
| 7,287,863 | B2* | 10/2007 | Liang | G02B 27/0994 |
| | | | | 353/122 |
| 8,403,527 | B2* | 3/2013 | Brukilacchio | G01N 21/8806 |
| | | | | 362/540 |
| 2003/0021124 | A1* | 1/2003 | Elbrecht | A61B 18/203 |
| | | | | 362/572 |
| 2003/0057443 | A1* | 3/2003 | Dietrich | G02B 6/4214 |
| | | | | 257/200 |
| 2004/0058553 | A1* | 3/2004 | Tanaka | G02B 27/0994 |
| | | | | 438/710 |
| 2004/0179807 | A1* | 9/2004 | Tanaka | G02B 27/0994 |
| | | | | 385/146 |
| 2004/0201898 | A1* | 10/2004 | Chang | G02B 27/0927 |
| | | | | 359/640 |
| 2005/0270793 | A1* | 12/2005 | Chang | G02B 27/0994 |
| | | | | 362/346 |
| 2007/0263298 | A1* | 11/2007 | El-Ghoroury | G03B 21/208 |
| | | | | 359/838 |
| 2012/0226268 | A1* | 9/2012 | Liu | A61N 5/0613 |
| | | | | 606/9 |
| 2013/0135710 | A1* | 5/2013 | Nagano | G02F 1/353 |
| | | | | 359/326 |
| 2015/0289934 | A1* | 10/2015 | Liu | A61B 18/203 |
| | | | | 606/9 |
| 2015/0313671 | A1* | 11/2015 | Liu | G02B 6/4268 |
| | | | | 606/9 |
| 2016/0310756 | A1 | 10/2016 | Boll et al. | |
| 2017/0276857 | A1* | 9/2017 | Vandenberg | G02B 27/0994 |

FOREIGN PATENT DOCUMENTS

| | | | | |
|---|---|---|---|---|
| CN | 102935012 | A | 2/2013 | |
| CN | 102940529 | A | 2/2013 | |
| CN | 103178432 | A | 6/2013 | |
| CN | 203423371 | U | 2/2014 | |
| CN | 103941406 | A | 7/2014 | |
| CN | 203988360 | U | 12/2014 | |
| CN | 104688337 | A | 6/2015 | |
| CN | 106621068 | A | 5/2017 | |
| CN | 206404189 | U | 8/2017 | |
| EP | 3219360 | A1 | 9/2017 | |
| KR | 102038941 | B1 * | 6/2019 | ............ A61B 18/20 |
| RU | 12887 | U1 | 2/2000 | |
| RU | 133723 | U1 | 10/2013 | |
| WO | WO-2011143663 | A2 * | 11/2011 | ............ A61B 90/98 |
| WO | 2016074300 | A1 | 5/2016 | |

* cited by examiner

SEMICONDUCTOR LASER MODULE AND METHOD FOR APPLICATION IN NONINVASIVE MEDICAL TREATMENT

The priority to a China patent application submitted to China Patent Office on Oct. 17, 2016, which application number is 201610901567.5 and which invention title is "A Semiconductor Laser Module and Method for Noninvasive Medical Treatment"; and the priority to a China patent submitted to China patent office on Oct. 17, 2016, which application number is 201621127578.4 and which invention title is: "A High-Power Semiconductor Laser Module for Noninvasive Medical Treatment" are claimed. Their all contents are recited and combined in this application.

TECHNICAL FIELD

The disclosure herein relates to the field of semiconductor lasers, particularly relates to a semiconductor laser module and a method for application in noninvasive medical treatment.

BACKGROUND

As important field of laser application, laser medical treatment and laser beauty have a very rapid development at present. A semiconductor laser has the characteristics: small size, light weight, long service life, and wide wavelength coverage. It is particularly suitable for medical beauty equipment. The application of the semiconductor laser in the area of medical beauty treatment mainly comprises removing hair, tendering skin, dissolving fat, etc.

Taking dissolving fat as an example, the dissolving fat scheme in the prior art mainly comprises the following three schemes:

Scheme 1: directly irradiate a fat part by an optical fiber coupling type laser. The disadvantage of the scheme is that the cost is high and the structure is complex.

Scheme 2: suck fat through an operation in a body. The purpose of reducing fat is achieved through directly stripping the fat in a body by a surgical operation. The disadvantage of the scheme is that there is trauma, the recovery is slow, and the risk is high.

Scheme 3: dissolve fat with ultrasonic wave. The purpose of reducing fat is achieved through focusing an ultrasonic wave in a fat layer inside a body, heating the fat, and causing the internal metabolism of the adipose tissues. The disadvantage of the scheme is that: the realization needs enough thickness of the fat layer, meanwhile, the focusing depth is not easy to control, and heating adipose tissues without distinction can cause risk of damaging nerve.

In consideration of the disadvantages of the above schemes, a laser medical method which does not cause trauma and which has remarkable effect is urgently needed.

SUMMARY

In view of the above, the main purpose of the present invention is to provide a semiconductor laser module and a method. The characteristics of the scheme is: based on a direct-output type semiconductor laser, using the technical scheme provided by the present invention, the purpose of treatment can be achieved by extracorporeal irradiation without causing any trauma on the human body; also, the cost is low and the treatment effect is good.

The technical scheme of the invention is as follows:

In the first aspect, an embodiment of the present invention provides a semiconductor laser module. The semiconductor laser module comprises: a direct-output type semiconductor laser light source, and a light beam shaping device disposed in the light-exit direction of the direct-output type semiconductor laser light source. The light beam shaping device comprises a light reflection component configured to homogenize the laser beam outputted by the direct-output type semiconductor laser light source.

Further, the light beam shaping device also comprises a lens. The lens is disposed between the direct-output type semiconductor laser light source and the light reflection component, and is used to carry out fast-axis and/or slow-axis beam expansion for the laser beam outputted by the direct-output type semiconductor laser light source.

Further, the light reflection component is a hollow component. The matrix material for the light reflection component comprises metal or plastic. The inner wall of the light reflection component is configured to achieve that the laser beam is reflected on the inner wall of the light reflection component, to form a uniform light path.

Further, a reflecting medium is plated on the inner wall of the light reflection component. The reflecting medium comprises metal.

Further, the cross section of the light reflection component is square, or circular, or polygonal. The cross-sectional area of the laser beam input end of the light reflection component is smaller than or equal to the cross-sectional area of the laser beam output end.

Further, the number of the lenses is one or more. The light reflection component is a reflecting bowl or a reflecting cover.

Further, the module also comprises a cooling structure. The cooling structure is disposed on the periphery of the light reflection component. The cooling structure comprises a cooling frame, a thermoelectric cooler and a heat dissipation block.

Here, the heat dissipation block is disposed on the periphery of the light reflection component. The heat dissipation block is configured to cool the light reflection component and the thermoelectric cooler. The thermoelectric cooler is configured to cool the cooling frame. The cooling frame is disposed on the periphery of the heat dissipation block. The thermoelectric cooler is disposed between the heat dissipation block and the cooling frame, and is in contact with the heat dissipation block and the cooling frame.

Further, a temperature sensor is disposed inside the cooling frame and is configured to sense the temperature information of the cooling frame. The sensed temperature information is sent to a control system, so that the control system adjusts the cooling amount of the thermoelectric cooler according to the temperature information.

Further, a contact window used for contacting skin and cooling the skin is disposed at the cooling frame. The cooling frame is used for cooling the contact window. A contact sensor is disposed at the contact window. The contact sensor is configured to sense the fit degree between the contact window and the skin.

Further, the module also comprises a fixing frame. One end of the fixing frame is connected with the direct-output type semiconductor laser light source. The fixing frame forms an accommodating space configured to accommodate the light beam shaping device.

Further, the other end of the fixing frame extends outwards to form a fixing platform. The cooling frame is disposed on the fixing platform. A mounting space is surrounded by the fixing platform, the cooling frame, and the light reflection component. The mounting space is configured to mount the heat dissipation block.

Further, the heat dissipation block comprises a cooling loop. The cooling loop comprises an inlet hole and an outlet hole. A through hole is disposed at the fixing platform. The inlet hole and the outlet hole penetrate through the through hole. The cooling loop is a liquid cooling loop. The inlet hole is configured to input a cooling liquid. The outlet hole is configured to output the cooling liquid.

Further, the module also comprise a sealing device configured to seal and support the semiconductor laser module.

Further, the sealing device is a hollow shell-shaped component. A light outlet is disposed at the sealing device. The light outlet is configured to apply the homogenized laser beam to a to-be-treated region in a way of extracorporeal irradiation.

In the second aspect, the embodiment of the invention provides a noninvasive medical treatment method. The method utilizes a direct-output type semiconductor laser. The direct-output type semiconductor laser comprises a semiconductor laser module described in the first aspect of the embodiment of the present invention. The method comprises:

The direct-output type semiconductor laser serves as a light source. The wavelength of the laser emitted by the light source corresponds to the absorption wavelength of tissues of the to-be-treated region. The laser acts on the to-be-treated region in a way of extracorporeal irradiation, to carry out a noninvasive treatment.

The technical scheme disclosed in the present invention uses the direct-output type semiconductor laser as a light source. The characteristic that a semiconductor laser has large divergence angle, is fully utilized. Noninvasive treatment is realized through large-area light spot irradiation outside a body. Through the technical scheme provided by the present invention, a very good treatment effect is achieved without causing any trauma on a human body. Noninvasive medical treatment is successfully realized. In view of cost, the high cost problem of a traditional optical fiber coupling type scheme is solved, by the scheme of the present invention which is based on the direct-output type semiconductor laser.

In addition, the effectiveness of space utilization is fully considered by the design of the structure and the position of the cooling structure of the semiconductor laser module. The volume of the laser treatment head is reduced. The problem that local skin temperature rises when laser therapy is carried out, is solved. User experience is improved.

In addition, the temperature sensor disposed on the cooling frame can monitor the temperature of the cooling frame in real time. The temperature is fed back to the control system. The control system adjusts the cooling amount of the thermoelectric cooler according to the feedback result, to achieve real-time temperature control and accurate temperature control.

BRIEF DESCRIPTION OF FIGURES

In order to clearly explain the technical schemes of the embodiments of the present invention, the figures which usage is needed in the embodiments are introduced briefly as follows. It should be understood that the following figures only show some embodiments of the present invention, thus, should not be regarded as limitation on the range. For a technical person with ordinary skills in the art, according to these figures, other related figures can be obtained without creative effort.

The explanation for main element symbols:
100—semiconductor laser module; 1—direct-output type semiconductor laser light source; 2—lens; 3—light reflection component; 4—cooling device; 5—sealing device; 6—fixing screw; 30—cooling structure; 31—cooling frame; 311—opening hole; 32—thermoelectric cooler; 33—heat dissipation block; 331—inlet hole; 332—outlet hole; 34—contact window; 35—contact sensor; 41—accommodating space; 40—fixing frame; 42—fixing platform; 421—screw hole; 422—through hole; 50—mounting space.

DETAILED DESCRIPTION

Through a semiconductor laser module provided by an embodiment of the present invention, a remarkable medical effect can be achieved without causing any trauma on a human body. The medical treatment described in the present invention may include but is not limited to dissolving fat, tendering skin, etc. Explanation is given in the embodiment of the present invention, taking noninvasive dissolving fat as an example.

The principle of the present invention is: a semiconductor laser with wavelength 700 nm-1550 nm, in particular, with wavelength 1064 nm, is selected (the absorption effect of the laser with the wavelength by adipose tissue is optimal. For another tissue, a semiconductor laser is selected which wavelength corresponds to the absorption wavelength of the tissue). Using characteristics of the semiconductor laser that the divergence angle is large, through a way of large-area light spot irradiation, the adipose tissue of a human body is irradiated intermittently. Thus, the temperature of the adipose tissue reaches a temperature at which the adipose tissue is emulsified. The adipose tissue is decomposed under the emulsifying temperature, and is further absorbed and discharged by the human body. The effect of noninvasive dissolving fat is achieved.

Figure 1:
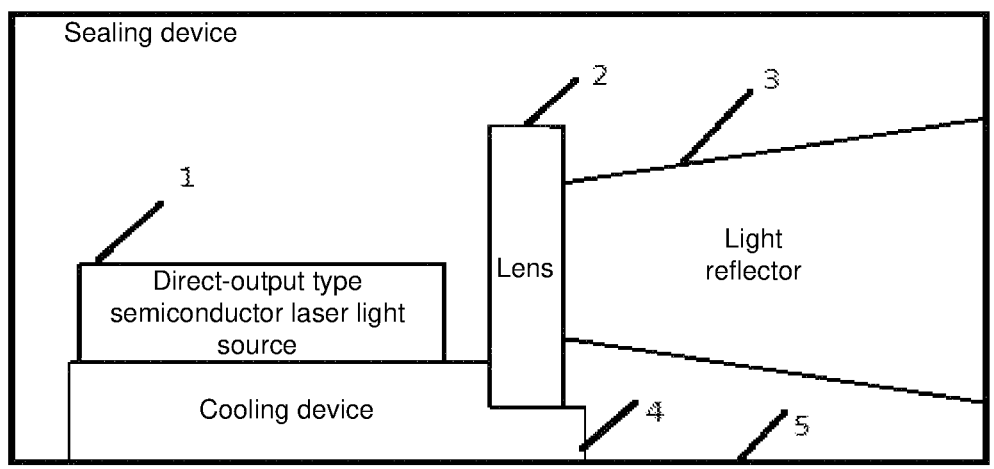
FIG. 1-FIG. 6 schematically show structural diagrams of a semiconductor laser module from different view angles, according to embodiments of the present invention.
Figure 2:
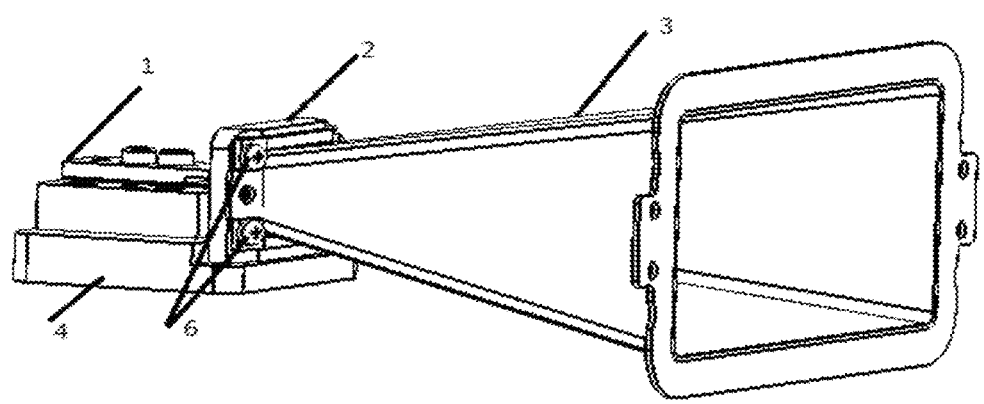
Figure 3:
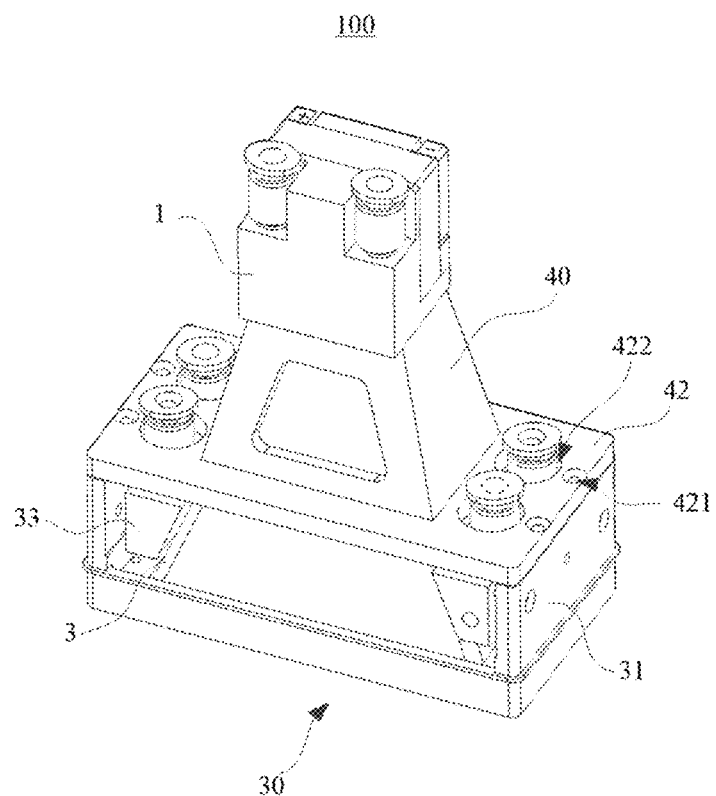
Figure 4:
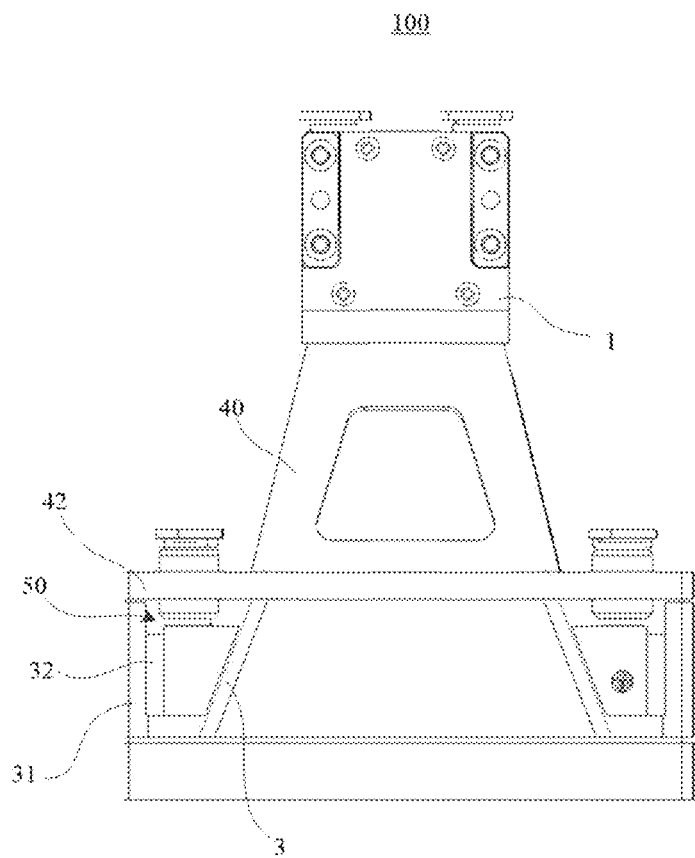
Figure 5:
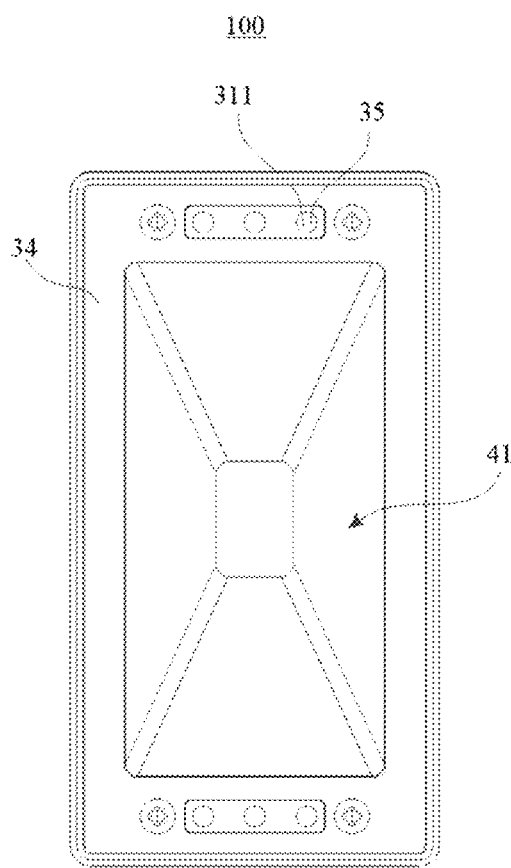
Figure 6:
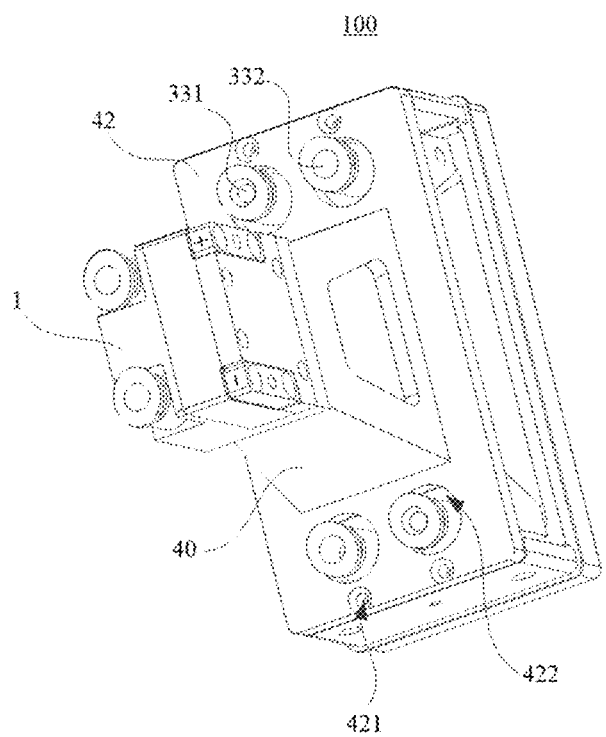

FIG. 1 is a schematic structural diagram of a semiconductor laser module 100 provided by an embodiment of the present invention. FIG. 2 is a schematic structural connection diagram of the semiconductor laser module 100 provided by an embodiment of the present invention. The direct-output type semiconductor laser light source 1 in the embodiment of the present invention may be a single-bar or multi-bar semiconductor laser, a single emitter or multi-single emitter semiconductor laser or other types of semiconductor lasers including but not limited to an edge emitting semiconductor laser light source or a surface emitting semiconductor laser light source, etc. The number of the lasers can be set as one or more according to actual needs. The semiconductor laser module 100 mainly comprises: a direct-output type semiconductor laser light source 1 configured to perform noninvasive treatment through emitting a laser beam which fast axis divergence angle is 0-80 degrees and which slow axis divergence angle is 0-15 degrees (the range of the fast axis divergence angle and the range of the slow axis divergence angle described here are only used for illustration). The noninvasive treatment is carried out in a way of extracorporeal irradiation.

The semiconductor laser module 100 further comprises a beam shaping device. Concretely, the light beam shaping device may comprise a lens 2 and a light reflection component 3. The lens 2 and the light reflection component 3 are sequentially disposed in the light-exit direction of the direct-output type semiconductor laser light source 1. The beam shaping device is configured to homogenize and expand the laser emitted by the direct-output type semiconductor laser light source 1.

Here, the light reflection component 3 is mainly used to homogenize the laser beam outputted by the direct-output type semiconductor laser light source 1. The homogenization may concretely be: shape a laser beam outputted by the direct-output type semiconductor laser light source which is in gaussian distribution into a laser beam which is in flat top distribution.

The lens 2 is disposed between the direct-output type semiconductor laser light source 1 and the light reflection component 3, and is used to perform fast-axis and/or slow-axis beam expansion for the laser beam outputted by the direct-output type semiconductor laser light source 1.

It should be noted that the arrangement of the lens 2 is not necessary. In other words: when the direct-output semiconductor laser light source 1 is a surface emitting semiconductor laser light source, because the fast axis divergence angle of the surface emitting semiconductor laser light source is in agreement with the slow axis divergence angle, so that the process of the fast axis and/or the slow axis expansion for the laser beam can be omitted. In other words, under such situation, the arrangement of the lens 2 can be omitted.

Further, when the direct-output type semiconductor laser light source 1 is an edge emitting semiconductor laser light source, in order to achieve a homogenized light spot with certain specific size requirement, the lens 2 can be arranged. The main usage is to perform slow-axis beam expansion for the laser beam outputted by the edge emitting semiconductor laser light source to obtain a homogenized light spot with the specific size. If there is no specific size requirement for the outputted homogenized light spot, the arrangement of the lens 2 can be omitted.

In practical application, the light reflection component 3 and the lens 2 are fixed together through a fixing screw 6. It should be noted that the number of the lenses 2 may be one or more. The specific number can be determined according to actual requirements. The lens 2 may be a general lens such as a cylindrical mirror, and may also be a diffraction device etc. A device, as long as the device can realize beam expansion effect for a laser beam, should be comprised in the scope of the present invention. The light reflection component 3 may include but not limited to any optical device such as a reflecting cover, a reflection bowl, etc., which can homogenize a laser beam.

Concretely, the light reflection component 3 may be a hollow component. The matrix material for the light reflection component 3 may include but not limited to: metal (such as stainless steel and nickel), or plastic etc. The inner wall of the light reflection component 3 may be configured to realize that the laser beam is reflected on the inner wall of the light reflection component, to form a homogenized light path.

Preferably, the inner wall of the light reflection component 3 may also be plated with a reflecting medium. The reflecting medium may include but not limited to any one or more kinds of medium materials such as metal (for example, gold), etc., which can realize light reflection.

As to the above, it should be noted that: because the inner wall of a light reflection component, which is made of some matrix materials (such as metal), has a reflecting characteristic, so that it is not necessary to plate reflecting medium on the inner part of the light reflection component.

Further, the cross section of the light reflection component 3 can be square, or round, or polygonal, etc. The cross-sectional area of the laser beam input end of the light reflection component 3 is smaller than or equal to the cross-sectional area of the laser beam output end. In other words, the caliber of the light reflection component 3, may gradually increase from the laser beam input end to the laser beam output end, may also be kept unchanged from the laser beam input end to the laser output end.

Further, the module may also comprise a cooling device 4. The cooling device 4 may be a liquid cooling type cooling device configured to dissipate heat for the direct-output type semiconductor laser light source 1 to guarantee that the direct-output type semiconductor laser light source 1 can normally continuously work.

Further, the module may also comprise a sealing device 5. The sealing device 5 is mainly used for sealing and supporting the semiconductor laser module. A screw hole is disposed at the light reflection component 3, and is configured to connect and fix the light reflection component 3 with the sealing device 5 together.

Concretely, the sealing device 5 is a hollow shell-shaped component. A light outlet is disposed at the sealing device 5. The light outlet is configured to apply the homogenized and expanded laser to the to-be-treated region in a way of extracorporeal irradiation. In practice, the sealing device 5 may be manufactured into various shapes according to requirements. It should be noted that in an example of noninvasive dissolving fat, the wavelength of the light beam emitted by the semiconductor laser module 100 is preferably selected as 1064 nm.

The semiconductor laser module 100 provided by the embodiment of the present invention further comprises a cooling structure 30. The cooling structure 30 is disposed on the periphery of the light beam shaping device, and is configured to cool the light beam shaping device and cool local skin heated. FIG. 3-FIG. 6 are schematic structural diagrams of the semiconductor laser module 100 provided by the embodiment of the prevent invention, from four view angles. The cooling structure 30 comprises a cooling frame 31, a thermoelectric cooler 32 and a heat dissipation block 33. Here, the heat dissipation block 33 is disposed on the periphery of the light beam shaping device. Concretely, the heat dissipation block 33 is disposed on the periphery of the light reflection component 3. The cooling frame 31 is disposed on the periphery of the heat dissipation block 33. The thermoelectric cooler 32 is disposed between the heat dissipation block 33 and the cooling frame 31, and is in contact with the heat dissipation block 33 and the cooling frame 31. The heat dissipating block 33 is configured to cool the light reflection component 3 and the thermoelectric cooler 32. The thermoelectric cooler 32 is configured to cool the cooling frame 31.

Here, a concrete contact or connection way among the cooling frame 31, the thermoelectric cooler 32 and the heat dissipation block 33 may be: a through hole structure may be disposed at the cooling frame 31; a structure having a threaded hole may be disposed at the heat dissipation block 33; the thermoelectric cooler 32 is clamped between the cooling frame 31 and the heat dissipation block 33; the cold surface of the thermoelectric cooler 32 is in contact with the cooling frame 31; the hot surface of the thermoelectric cooler 32 is in contact with the heat dissipation block 33; and finally a screw can be used to penetrate through the through hole in the cooling frame 31 and the threaded hole in the heat dissipation block 33. Thus, the contact or connection among the three components is realized.

The cooling frame 31 is connected with the contact window 34. The contact window 34 is configured to be in contact with skin of a human body. The contact window 34, on the one hand, can flatten the skin to guarantee full contact and uniform irradiation; on the other hand, can cool the skin based on the cooling frame 31. In order to ensure rapid cooling, the material for the contact window 34 needs to have high thermal conductivity. In the embodiment, the contact window 34 may be made of sapphire.

In the embodiment, the semiconductor laser module 100 may further comprise a fixing frame 40 to fix the light beam shaping device and the cooling structure 30. Here, one end of the fixing frame 40 is connected with the direct-output type semiconductor laser light source 1. The fixing frame 40 forms an accommodating space 41. The accommodating space 41 may be surrounded by the frame of the fixing frame 40. The accommodating space 41 is configured to accommodate the beam shaping device. For example, a reflecting cover or a reflecting bowl of the light beam shaping device can be contained in the accommodating space 41.

The working principle of the cooling structure 30 provided by the embodiment is:

The heat dissipation block 33 is in contact with the beam shaping device and the thermoelectric cooler 32, to cool the light beam shaping device and the thermoelectric cooler 32. The thermoelectric cooler 32 is configured to cool the cooling frame 31. Because the cooling frame 31 is directly connected with the contact window 34, the contact window 34 is rapidly cooled. The contact window 34 is in contact with the skin. Therefore, rapid cooling for the skin of the to-be-treated region is achieved.

The embodiment has no limit for cooling way of the heat dissipation block 33. In the embodiment, a cooling loop is disposed in the heat dissipation block 33. The cooling loop comprises an inlet hole 331 and an outlet hole 332. The inlet hole 331 is connected with the outlet hole 332. The cooling loop may achieve cooling effect through cooling gas or liquid. In the embodiment, the cooling loop performs cooling by introducing cooling liquid. Concretely, the inlet hole 331 is configured to input a cooling liquid. The outlet hole 332 is configured to output the cooling liquid. The cooling liquid entering the cooling loop through the inlet hole 331 takes away the heat of the heat dissipation block 33 and then flows out of the cooling loop through the outlet hole 332. Thus, cooling effect is achieved. In order to enhance the heat dissipation effect of the heat dissipation block 33, to make the heat dissipation block 33 be more easily cooled, material with high heat conductivity is selected for the heat dissipation block 33. It should be noted that the embodiment has no limit that the position and the number of the inlet holes 331 and the outlet holes 332 of the heat dissipation block 33 are uniquely defined. Above is only used for illustration and explanation.

The cooling frame 31 is mounted on the fixing frame 40. Concretely, the other end of the fixing frame 40 extends outwards to form a fixing platform 42. The cooling frame 31 is mounted on the fixing platform 42. For example, a screw hole 421 may be formed at the fixing platform 42. The cooling frame 31 is fixed on the fixing platform 42 through the cooperation between the bolt and the screw hole 421.

A mounting space 50 is surrounded by the fixing platform 42, the cooling frame 31 and the beam shaping device. The mounting space 50 is configured to mount the heat dissipation block 33. It is easily understood that the number of the mounting spaces 50 can be more than one. For example, the number of the heat dissipation blocks 33 is two; the number of the mounting spaces 50 is two; each mounting space 50 contains a heat dissipation block 33. The heat dissipation block 33 is mounted in the mounting space 50, so that the space is maximumly utilized. The layout is reasonable, so that the volume of the laser treatment head is small. It is convenient for operation.

A through hole 422 may also be disposed at the fixing platform 42, and be disposed relatively to the inlet hole 331 and the outlet hole 332 of the heat dissipation block 33, so that it is convenient for the inlet hole 331 and the outlet hole 332 pass through the through hole 422, and it is convenient to connect pipes to transport cooling liquid. It is easily understood that, the embodiment has no limit on the number of the through holes 422, which is in agreement with the number of the inlet holes 331 and the outlet holes 332.

In addition, a temperature sensor is disposed on the cooling frame 31 (not shown in the figure). The temperature sensor is configured to sense the temperature information of the cooling frame 31. The sensed temperature information is sent to a control system. The control system may be a control system of the semiconductor laser module 100, so that the control system can adjust the cooling amount of the thermoelectric cooler 32 according to the temperature information. For example, when the temperature of the thermoelectric cooler 32 is too low, the cooling amount of the heat dissipation block 33 is reduced; so that the temperature of the thermoelectric cooler 32 is controlled to rise. The temperature sensor may be disposed inside the part of the cooling frame 31 which contacts skin.

In addition, a contact sensor 35 is disposed at the contact window 34, and is configured to sense the fit degree between the contact window 34 and skin of a human body, so as to detect whether the treatment head is in tight contact with the skin of the human body. Concretely, an opening hole 311 is disposed at the cooling frame 31. The contact sensor 35 is disposed inside the opening hole 311. The embodiment has no limit on the position and the number of the opening holes 311.

In summary, the semiconductor laser module provided by the embodiment of the present invention, mainly comprises a direct-output type semiconductor laser light source, a light beam shaping device, and a cooling structure etc. The light beam shaping device is disposed in the light-exit direction of the direct-output type semiconductor laser light source. The cooling structure comprises a cooling frame, a thermoelectric cooler and a heat dissipation block. The heat dissipation block is disposed on the periphery of the light beam shaping device. The heat dissipation block cools the cooling frame through the thermoelectric cooler, to cool the contact window which is in contact with skin. The semiconductor laser module provided by the embodiment of the present invention fully takes efficient utilization of space into account and reduces the volume of the laser treatment head, through the design of the structure and the position for the heat dissipation block, the thermoelectric cooler, and the cooling frame. The problem that local skin temperature rises when laser therapy is performed, is solved. User experience is improved.

In addition, a temperature sensor is disposed at the cooling frame, and can monitor the temperature of the cooling frame in real time. The temperature monitored is fed back to the control system. The control system adjusts the cooling amount of the thermoelectric cooler according to the feedback result. Real-time temperature control and accurate temperature control are achieved.

In addition, the embodiment of the present invention further provides a method for noninvasive medical treatment. The method utilizes a direct-output type semiconductor laser. The direct-output type semiconductor laser comprises the semiconductor laser module described in the above embodiment. The method comprises:

Step S1, a direct-output type semiconductor laser serves as a light source. The wavelength of the laser corresponds to the absorption wavelength of tissues of to-be-treated region;

Here, the direct-output type semiconductor laser light source may emit a laser beam with a certain divergence angle. For example, the fast axis divergence angle of the laser beam is 0-80 degrees, the slow axis divergence angle of the laser beam is 0-15 degrees (the range of the fast axis divergence angle and the range of the slow axis divergence angle are only used for illustration, without limiting the scheme).

Moreover, the "direct-output type semiconductor laser" described in the embodiments of the present invention, may include but not limited to an edge emitting semiconductor laser light source, or a surface emitting semiconductor laser light source, etc.

Step S2, the laser is applied to a to-be-treated region in a way of extracorporeal irradiation, to perform noninvasive treatment.

The above description is only preferred embodiments of the present invention, and is not used for limiting the protection scope of the present invention. For those skilled in the art, the invention may have various modifications and changes. Any modifications, equivalent replacements, improvements, etc., within the spirit and principle of the present invention shall fall within the scope of protection of the present invention.

The industrial practicability of the present invention: The invention can achieve good laser treatment effect without causing any trauma on a human body. Noninvasive medical treatment is achieved. Meanwhile, the manufacturing cost is low.

What is claimed is:

1. An apparatus comprising: a direct-output type semiconductor laser light source, a light reflector, a cooling structure disposed on a periphery of the light reflector and a fixing frame;
   wherein the light reflector comprises a hollow interior space, a first opening receiving a laser beam from the direct-output type semiconductor laser light source into the hollow interior space, a second opening from which the laser beam exits from the hollow interior space;
   wherein the hollow interior space has a reflective surface between the first opening and the second opening;
   wherein a cross-sectional area of the first opening is smaller than a cross-sectional area of the second opening;
   wherein the first opening is smaller in both dimensions thereof than the second opening;
   wherein the cooling structure comprises a cooling frame, a thermoelectric cooler and a heat dissipation block;
   wherein the heat dissipation block has a cooling loop therein configured to accommodate flow of a cooling liquid, and is in direct thermal contact with the light reflector and the thermoelectric cooler;
   wherein the thermoelectric cooler is in direct thermal contact with the cooling frame and is configured to transfer heat from the cooling frame to the heat dissipation block;
   wherein one end of the fixing frame is directly connected with the direct-output type semiconductor laser light source;
   wherein a portion of the light reflector is in an interior of the fixing frame;
   wherein the other end of the fixing frame has a fixing platform; and
   wherein the cooling frame is disposed on the fixing platform.

2. The apparatus of claim 1, further comprising a lens between the direct-output type semiconductor laser light source and the light reflector and configured to expand the laser beam along a fast axis or a slow axis of the laser beam.

3. The apparatus of claim 1, wherein the reflective surface is a layer of metal.

4. The apparatus of claim 1, wherein a cross-sectional shape of the first opening or the second opening is square, round, or polygonal.

5. The apparatus of claim 1, wherein the light reflector is a reflecting bowl or a reflecting cover.

6. The apparatus of claim 1, further comprising a temperature sensor and a control system; wherein the temperature sensor is disposed inside the cooling frame and is configured to sense a temperature of the cooling frame; wherein the control system is configured to adjust power of the thermoelectric cooler based on the temperature.

7. The apparatus of claim 1, further comprising a contact window on the cooling frame, configured to contact a skin and to cool the skin; wherein the cooling frame configured to cool the contact window; wherein the apparatus further comprises a contact sensor at the contact window; wherein the contact sensor is configured to sense a degree of contact between the contact window and the skin.

8. The apparatus of claim 1, wherein the cooling loop comprises an inlet hole and an outlet hole; wherein the fixing platform comprises a through hole; wherein the inlet hole and the outlet hole extend through the through hole.

9. A method of using the apparatus of claim 1, comprising: directing the laser beam exiting the second opening toward a region on a patient; wherein the laser beam is at a wavelength that tissues in the region absorb.

10. The apparatus of claim 1, wherein the light reflector is configured to shape the laser beam from a Gaussian beam into a flat top beam.

* * * * *